US012135305B2

(12) United States Patent
Nakatani (10) Patent No.: US 12,135,305 B2
(45) Date of Patent: Nov. 5, 2024

(54) BIOSENSOR AND MEASUREMENT METHOD USING THE SAME

(71) Applicant: ARKRAY, Inc., Kyoto (JP)

(72) Inventor: Ayano Nakatani, Kyoto (JP)

(73) Assignee: ARKRAY, INC., Kyoto (JP)

( * ) Notice: Subject to any disclaimer, the term of this patent is extended or adjusted under 35 U.S.C. 154(b) by 839 days.

(21) Appl. No.: 17/214,570

(22) Filed: Mar. 26, 2021

(65) Prior Publication Data
US 2021/0302350 A1  Sep. 30, 2021

(30) Foreign Application Priority Data

Mar. 27, 2020 (JP) .................................. 2020-058700
Feb. 18, 2021 (JP) .................................. 2021-024146

(51) Int. Cl.
*G01N 27/327* (2006.01)
*C12N 9/04* (2006.01)
*G01N 27/30* (2006.01)
*G01N 27/49* (2006.01)

(52) U.S. Cl.
CPC ....... *G01N 27/3271* (2013.01); *C12N 9/0006* (2013.01); *G01N 27/49* (2013.01); *C12Y 101/05* (2013.01); *G01N 27/30* (2013.01)

(58) Field of Classification Search
None
See application file for complete search history.

(56) References Cited

U.S. PATENT DOCUMENTS

| 2007/0034512 | A1  | 2/2007 | Yamaoka et al. |
| 2008/0248354 | A1* | 10/2008 | Kubo ........................ C12Q 1/004 |
| | | | 429/458 |
| 2010/0200538 | A1* | 8/2010 | Petisce ...................... B81C 1/00539 |
| | | | 216/13 |
| 2011/0186428 | A1  | 8/2011 | Beaty et al. |
| 2016/0169827 | A1  | 6/2016 | Hochstetler et al. |
| 2017/0184534 | A1  | 6/2017 | Goodwin et al. |
| 2020/0386707 | A1  | 12/2020 | Funahashi et al. |

FOREIGN PATENT DOCUMENTS

| JP | 2013-518264 A  | 5/2013 |
| JP | 2018-503080 A  | 2/2018 |
| WO | WO-0073785 A2 * | 12/2000 ............. C12Q 1/002 |
| WO | 2015/060119 A1 | 4/2015 |
| WO | 2019/117092 A1 | 6/2019 |
| WO | 2019/204578 A1 | 10/2019 |

OTHER PUBLICATIONS

Office Action issued in the corresponding EP Application No. 21164644.3, dated Sep. 12, 2023.
Extended European Search Report issued in corresponding European Patent Application No. 21164644.3 dated Aug. 31, 2021.

* cited by examiner

*Primary Examiner* — J. Christopher Ball (74) *Attorney, Agent, or Firm* — Morgan, Lewis & Bockius LLP (57) ABSTRACT

There is provided a biosensor for measuring a measuring target substance in a sample comprising an insulating substrate, an electrode pair provided on the insulating substrate, and a reagent that includes an oxidoreductase and an electron transfer substance and is provided at least on a working electrode of the electrode pair, wherein the working electrode is composed of one or more kinds of nickel alloys selected from the group consisting of a nickel-ruthenium alloy, a nickel-tungsten alloy, and a nickel-vanadium alloy.

12 Claims, 6 Drawing Sheets

BIOSENSOR AND MEASUREMENT METHOD USING THE SAME

TECHNICAL FIELD

This disclosure relates to a biosensor and a measurement method using the same.

BACKGROUND ART

A biosensor generally includes an electrode provided with a reagent containing an oxidoreductase and an electron transfer substance, and carbon, gold, palladium, or the like is commonly used as an electrode material. Carbon is inexpensive, however there are drawbacks in that it requires screen printing, and it is not easy to control the fluctuation of the resistance value dependent on the environment during the manufacture of an electrode. Meanwhile, with respect to a noble metal such as gold and palladium, although high precision electrode processing is easy, it is more expensive than carbon. Although use of a base metal (a metal with ionization tendency greater than hydrogen) as an electrode is attractive in terms of low price and easy processing, there are drawbacks in that a base metal deteriorates fast, and easily dissolves out when a voltage is applied.

Patent Literature 1 to 3 disclose the use of a nickel-chromium alloy, a nickel-copper alloy, or the like, which is a base metal alloy, as an electrode material of a biosensor. However, there has been room for improvement in terms of responsiveness to a component in a reagent such as an electron transfer substance, and reduction of a background current.

[Patent Literature 1] Japanese National-Phase Publication No. 2018-503080
[Patent Literature 2] International Publication No. WO2015060119
[Patent Literature 3] Japanese National-Phase Publication No. 2013-518264

SUMMARY OF INVENTION

An aspect of the present invention is to provide a biosensor that can be produced inexpensively and easily, and can measure the concentration of a measuring target substance such as glucose with high reproducibility.

The inventors diligently conducted investigation. As a result, it has been found that, by using a specific nickel alloy as the electrode material for the working electrode in a biosensor in which a reagent containing an oxidoreductase and an electron transfer substance is provided at least on the working electrode, although it is made of a base metal alloy, a biosensor that exhibits responsiveness to the electron transfer substance close to that of a noble metal electrode, can be inexpensively and easily produced.

An aspect of the present invention relates to a biosensor for measuring a measuring target substance in a sample comprising an insulating substrate, an electrode pair provided on the insulating substrate, and a reagent that comprises an oxidoreductase and an electron transfer substance and is provided at least on a working electrode of the electrode pair, wherein the working electrode is composed of one or more kinds of nickel alloys selected from a nickel-vanadium alloy, a nickel-tungsten alloy, and a nickel-ruthenium alloy.

Another aspect of the present invention relates to a method for measuring a measuring target substance comprising supplying a sample containing the measuring target substance to the electrode pair mounted on the aforedescribed biosensor; applying a voltage between the pair of electrodes; measuring the value of a current flowing between the pair of electrodes; and calculating the amount of the measuring target substance based on the measured current value.

By using a specific nickel alloy for the working electrode of the biosensor, it is possible to obtain the responsiveness to an electron transfer substance close to that of a noble metal electrode. This makes it possible to inexpensively and easily produce a biosensor that can measure a measuring target substance such as glucose with high reproducibility.

BRIEF DESCRIPTION OF DRAWINGS

\* Sudden decrease in the response current value occurred within 5 sec
x Premature hike in the response current value occurred within 5 sec
Δ The variation of the 5-sec values of the response current value is 20 µA or more.
○ problem

DESCRIPTION OF EMBODIMENTS

Embodiments of the invention will be explained below. In this regard, the numerical range described as "A to B" means A or more and B or less.

(Biosensor)

The biosensor according to an embodiment of the present invention is a biosensor comprising an insulating substrate, an electrode pair provided on the insulating substrate, and a reagent provided at least on a working electrode of the electrode pair, wherein the working electrode is composed of one or more kinds of nickel alloys (hereinafter sometimes referred to as Ni alloys) selected from the group consisting of a nickel-vanadium alloy (Ni—V alloy), a nickel-tungsten alloy (Ni—W alloy), and a nickel-ruthenium alloy (Ni—Ru alloy). The biosensor is for measuring a measuring target substance in a sample wherein the sample is supplied to the electrode pair and the measuring target substance is measured by using the reagent.

(Electrode Pair)

The electrode pair in the biosensor according to an embodiment of the present invention includes a working electrode and a counter electrode, while there is no particular restriction on the number of electrodes. For example, the biosensor according to an embodiment of the present invention may include 3 electrode-system electrodes including a reference electrode in addition to the electrode pair consisting of a working electrode and a counter electrode. The biosensor according to an embodiment of the present invention may also include, in addition to the electrode pair consisting of a working electrode and a counter electrode (hereinafter, may be called as the first electrode pair), an additional electrode pair including a working electrode and a counter electrode for measuring a physical value other than the measuring target substance such as a value with respect to another measuring target substance in the sample, the temperature of the sample, or the like (hereinafter, may be called as the second electrode pair).

A nickel alloy can be used for the working electrode, and in embodiment of the present invention, one or more kinds of nickel alloys selected from the group consisting of a nickel-vanadium alloy, a nickel-tungsten alloy, and a nickel-ruthenium alloy are used.

The weight ratio of nickel to vanadium in the nickel-vanadium alloy is preferably from 80/20 to 95/5, more preferably from 85/15 to 95/5, further preferably from 90/10 to 94/6, and most preferably 92/8.

The weight ratio of nickel to tungsten in the nickel-tungsten alloy is preferably from 70/30 to 90/10, more preferably from 75/25 to 85/15, further preferably from 80/20 to 82/18, and most preferably 81/19.

The weight ratio of nickel to ruthenium in the nickel-ruthenium alloy is preferably from 60/40 to 40/60, more preferably from 55/45 to 45/55, further preferably from 52/48 to 48/52, and most preferably 50/50.

There is no particular restriction on the electrode material for the counter electrode, and for example, a metal electrode such as platinum, or a carbon electrode may be used. Further, a silver/silver chloride electrode may be used as the counter electrode, or a nickel alloy electrode as described above may also be used as the counter electrode. Preferably, the same nickel alloy as the working electrode can be used as the counter electrode because it can be produced inexpensively and easily.

There is no particular restriction on the electrode material for another electrode such as the reference electrode, and for example, a metal electrode such as platinum, or a carbon electrode, a silver/silver chloride electrode, a normal hydrogen electrode, a calomel electrode, and a palladium/hydrogen electrode, or the like may be used. Preferably, the same nickel alloy as the working electrode can be used as another electrode such as the reference electrode because it can be produced inexpensively and easily.

In the case that the biosensor according to an embodiment of the present invention has the first electrode pair and the second electrode pair as described above, the materials for the first electrode pair and the second electrode pair can be those for the first electrode pair and the second electrode pair as explained above, respectively. Preferably, all the working electrode and the counter electrode for the first electrode pair and the working electrode and the counter electrode for the second electrode pair may be the same nickel alloy because it can be produced inexpensively and easily.

(Substrate)

Electrodes, including the electrode pair, are provided on a substrate, and an insulating substrate is used as the substrate. There is no particular restriction on the type of an insulating substrate, and it may be made of an insulating material, such as various thermoplastic resins including polyetherimide (PEI), poly(ethylene terephthalate) (PET), and polyethylene (PE), thermosetting resins including a polyimide resin and an epoxy resin, glass, ceramic, and paper. From the viewpoint of enhancement of the fixing strength of an electrode, or a contact metal described below onto the substrate, a material with a Ra value, which is the arithmetic mean roughness of the surface, of 1 μm or more is preferable. In the case of a substrate with an Ra value of less than 1 μm, the surface is so smooth that the adhesiveness of an electrode or a contact metal becomes low. Although the size and thickness of the electrodes and the substrate may be set as needed, particularly the thickness of the electrode is preferably from 1 μm to 100 μm.

(Contact Metal)

Electrodes including an electrode pair are provided as a layer on the substrate, and it is preferable to provide a contact metal layer between the substrate and an electrode layer. In a case where a nickel alloy is placed on the insulating substrate, when an external force is applied to a biosensor, or a voltage is applied, the nickel alloy may be detached from the insulating substrate, or pores may emerge in the nickel alloy. Therefore, it is preferable to provide a contact metal for increasing the adhesive strength of the nickel alloy to the insulating substrate.

When only the working electrode is made of a nickel alloy in the biosensor of the present invention, a contact metal can be layered between the working electrode and the substrate. When both the working electrode and the counter electrode are made of a nickel alloy in the biosensor according to an embodiment of the present invention, a contact metal can be layered between the working electrode and the substrate and between the counter electrode and the substrate.

There is no particular restriction on the kind of the contact metal, insofar as a nickel alloy constituting an electrode can be strongly fixed to the substrate, and it is composed of, for example, titanium, molybdenum, tungsten, chromium, or iron, and preferably composed of titanium. Although the thickness of the contact metal may be set as appropriate, from the viewpoint of fixing strength, it is preferably from 5 μm to 100 μm, and for avoiding the influence of the ruggedness of the substrate, the total thickness of the nickel alloy and the contact metal is preferably from 10 μm to 55 μm.

In a case where the electrode is made of a nickel-vanadium alloy, and the contact metal is made of titanium, it is preferable to satisfy the following conditions, where the thickness of the titanium is represented by x, and that of the nickel-vanadium alloy by y.

(1) 7 μm≤x≤52 μm
(2) 3 μm≤y≤25 μm
(3) y=−11/16x+155/4

(Reagent)

In the biosensor according to an embodiment of the present invention, the reagent is provided at least on the working electrode of the electrode pair.

Although there is no particular restriction on the position on the working electrode where the reagent is provided, it is preferably at or near the terminal different from the terminal to be connected with a power supply for applying a voltage to the working electrode.

The reagent may be provided on both the working electrode and the counter electrode that constitute the electrode pair, or may also be provided on the working electrode, or on the substrate around the working electrode or the working electrode and the counter electrode, or also on a part of the substrate between the working electrode and the counter electrode. The reagent is preferably provided continuously on the working electrode, and is preferably provided in a thick layered structure. When the biosensor according to an embodiment of the present invention comprises the second electrode pair comprising a working electrode and a counter electrode for measuring a physical value other than the measuring target substance in addition to the first electrode pair comprising a working electrode and a counter electrode for measuring the measurement target substance, a reagent may be provided, or not provided on the second electrode pair. For example, when the physical value other than the measuring target substance is a hematocrit value, it may be a structure in which a portion of the reagent is loaded solely on the counter electrode as disclosed in International Publication No. WO2005/103669, or a structure in which no reagent is loaded as disclosed in Japanese Patent Laid-Open No. 2019-035748.

Although there is no particular restriction on a reagent included in the reagent, insofar as it is a reagent to be used for a detection reaction of a measuring target substance, the reagent contains at least an oxidoreductase and an electron transfer substance.

(Oxidoreductase)

An oxidoreductase is applicable insofar as it is an enzyme that uses a measuring target substance as a substrate, and can oxidize or reduce the measuring target substance. Examples thereof include an oxidoreductase containing at least one of pyrroloquinoline quinone (PQQ) and flavin adenine dinucleotide (FAD) as a catalytic subunit or a catalytic domain.

In a case where the measuring target substance is glucose, for example, glucose dehydrogenase or a glucose oxidase can be used, and specific examples of the glucose dehydrogenase include PQQ glucose dehydrogenase (PQQGDH), cytochrome glucose dehydrogenase (CyGDH) having an alpha subunit containing FAD. An example may include glucose-3-dehydrogenase derived from *Agrobacterium tumefaciens*.

The oxidoreductase may contain an electron transfer subunit, or an electron transfer domain. In a case where the measuring target substance is glucose, examples of the electron transfer subunit include a subunit including a heme having a function of electron transfer. Examples of an oxidoreductase containing the subunit including a heme include those containing cytochrome, and for example, glucose dehydrogenase containing cytochrome, or a fusion protein of PQQGDH and cytochrome may be used. In this regard, a fusion protein of PQQGDH and cytochrome has been disclosed, for example, in International Publication No. WO2005/030807.

In the case of a measuring target substance other than glucose, examples of an oxidoreductase include cholesterol oxidase, quinoheme ethanol dehydrogenase (QHEDH (PQQ Ethanol dh)), sorbitol dehydrogenase (Sorbitol DH), D-fructose dehydrogenase (Fructose DH), cellobiose dehydrogenase, lactate dehydrogenase, and urate oxidase.

Therefore, the biosensor according to an embodiment of the present invention can be used not only as a glucose sensor, but also as a cholesterol sensor, an ethanol sensor, a sorbitol sensor, a fructose sensor, a cellobiose sensor, a lactate sensor, a urate sensor, etc.

(Electron Transfer Substance)

An electron transfer substance to be contained in a reagent is a substance that can receive an electron generated by a reaction between a measuring target substance and the oxidoreductase, and can transfer the electron to an electrode, and is also called a mediator.

There is no particular restriction on the electron transfer substance, insofar as it is a compound that has no catalytic effect but is reduced by receiving electrons from an oxidoreductase, and re-oxidized at the electrode. Examples thereof include a ruthenium complex, a ferricyanide (also called hexacyanoferrate(III)) such as potassium ferricyanide, a quinone compound (e.g., 1,4-naphthoquinone, VK3, 9,10-phenanthrenequinone, 1,2-naphthoquinone, p-xyloquinone, methylbenzoquinone, 2,6-dimethylbenzoquinone, sodium 1,2-naphthoquinone-4-sulfonate, 1,4-anthraquinone, tetramethylbenzoquinone, thymoquinone, 1,2-naphthoquinone-4-sulfonate, 1,4-Anthraquinone, tetramethylbenzoquinone, and thymoquinone), a phenylenediamine compound (e.g., N,N-Dimethyl-1,4-phenylenediamine, and N,N,N',N-tetramethyl-1,4-phenylenediamine dihydrochloride), 1-methoxy-PMS (1-methoxy-5-methylphenazinium methyl sulfate), Coenzyme Q0, Azure A chloride, phenosafranin, 6-aminoquinoxaline, and tetrathiafulvalene. These may be used singly or in combination of two or more kinds thereof.

As the ruthenium complex, a ruthenium complex consisting of trivalent ruthenium (Ru(III)) and its ligand is preferable, and a ruthenium ammonia complex as shown below is more preferable.

$$[Ru(NH_3)_5X]^{n+}.$$

Here, examples of X include $NH_3$, a halogen ion, CN, pyridine, nicotinamide, bipyridine, and $H_2O$. Among these, $NH_3$ or a halogen ion (e.g., $Cl^-$, $F^-$, $Br^-$, or $I^-$) is preferable. The $n^+$ in the above Formula represents the valence of the oxidized ruthenium (III) complex and is determined properly according to the kind of X. The details of the ruthenium complex are disclosed in Japanese Patent Laid-Open No. 2018-013400.

Although the content of an oxidoreductase in the reagent of the biosensor according to an embodiment of the present invention may be determined as appropriate depending on the kind of the measuring target substance, since it is necessary that an oxidoreductase sufficient for the measuring target substance should be contained. The amount of an oxidoreductase is preferably from 1 to 10 U, more preferably from 1 to 5 U, and especially preferably from 1 to 3 U per 1 $cm^2$ of the surface area of the part where the reagent is provided on the biosensor.

The content of an electron transfer substance in the reagent is preferably higher than that of an oxidoreductase, and can be determined properly according to the kind of a measurement sample, etc. For example, it is preferably from 10 mmol to 100 mmol, more preferably from 10 mmol to 50 mmol, and especially preferably from 15 mmol to 20 mmol, per 1 $cm^2$ of the surface area of the part of a biosensor on which the reagent is provided.

(Other Components)

The reagent contains an oxidoreductase and an electron transfer substance, and in addition to these, a resin binder such as a butyral resin-type or a polyester resin-type, a binder such as a layered inorganic compound disclosed in Re-publication of PCT International Publication No. 2005/043146, or a surfactant may be contained.

The reagent may additionally contain additives such as a buffer, and a surfactant. As a buffer, an amine buffer, such as Tris, ACES, CHES, CAPSO, TAPS, CAPS, Bis-Tris, TAPSO, TES, Tricine, and ADA, may be used, or a phosphate buffer or a buffer having a carboxyl group such as a citrate buffer, a phosphate citrate buffer, an acetic acid-Na acetate buffer, a malic acid-Na acetate buffer, a malonic acid-Na acetate buffer, and a succinic acid-Na acetate buffer, may be used. The pH of the buffer is preferably from 6.8 to 7.2, and more preferably a pH of about 7.0.

Among these, use of a citrate buffer or a phosphate citrate buffer is preferable.

The molar concentration of a citrate in a citrate buffer, or a phosphate citrate buffer in the reagent in the part where the reagent is provided on the working electrode is preferably from 1.5 $\mu mol/cm^2$ to 22 $\mu mol/cm^2$, and particularly preferably from 7.5 $\mu mol/cm^2$ to 15 $\mu mol/cm^2$. When a sample is supplied to such an electrode pair of the biosensor, and the reagent is dissolved by the sample, the citrate concentration in the mixed solution of the reagent and the sample on the working electrode before diffusion is from approximately 20 mM to approximately 300 mM in the case of the reagent containing 1.5 $\mu mol/cm^2$ to 22 $\mu mol/cm^2$ of citrate, and from approximately 100 mM to approximately 200 mM in the case of the reagent containing 7.5 $\mu mol/cm^2$ to 15 $\mu mol/cm^2$ of citrate. In this regard, the mixed solution of the reagent and the sample on the working electrode means a solution present in a region where the reagent and a measuring target substance react on the working electrode, including the mixed solution physically present on the working electrode. Meanwhile, the mixed solution is a fluid in which there is a concentration gradient, and therefore the citrate concentration value here refers to the average concentration.

Examples of the surfactant include Triton X-100, sodium dodecyl sulfate, perfluorooctanesulfonic acid, sodium stearate, an alkylaminocarboxylic acid (or its salt), carboxybetaine, sulfobetaine, and phosphobetaine.

The biosensor may comprise in addition to the substrate, the contact metal, the electrode pair, and the reagent, a cover provided on the side of the substrate having the electrode pair for covering the electrode, a spacer provided between the substrate and the cover for forming a predetermined space between the substrate and the cover, and a sample supply port that is provided over a region including a reagent loading section of at least the working electrode of the electrode pair, and has a predetermined space. The sample supply port may be formed by processing the cover or spacer.

The biosensor may further comprise a member other than the above.

An example of a biosensor that can be used in one embodiment of the present invention is described below based on FIG. 1.

Panels (a) to (f) are perspective views showing a series of steps of producing a biosensor. However, a biosensor that can be used in an embodiment of the present invention is not limited to the following embodiments. For example, although the embodiment shown below uses a contact metal, a contact metal is not an indispensable constituent in the biosensor according to an embodiment of the present invention.

As shown in Panel (f) of FIG. 1, the biosensor A comprises a substrate 10, an electrode system (Panel (b) of FIG. 1) constituted with a counter electrode 11 having a first terminal, a second terminal that is connected to the measurement device described below, and a lead section that connects the first terminal to the second terminal, and the working electrode 12 having a first terminal that is adjacent to the first terminal of the counter electrode 11, a second terminal that is connected to the measurement device described below, and a lead section that connects the first terminal to the second terminal, a contact metal 19 (Panel (a) of FIG. 1) formed between the substrate 10 and the electrode system, an insulating layer 14, a spacer 15 having an opening, and a cover 16 with a through hole 18. As shown in Panel (c) of FIG. 1, a reagent 13 is provided on the first terminal of the working electrode 12. On top of the substrate 10, the insulating layer 14 is laminated on the lead sections of the electrode pair as shown in Panel (d) of FIG. 1. On top of the insulating layer 14, the spacer 15 having an opening at a position corresponding to a region including the first terminal, which is the part provided with the reagent of the working electrode 12, and the first terminal of the counter electrode opposing thereto, is provided as shown in Panel (e) of FIG. 1. In addition, on top of the spacer 15, a cover 16 having a through hole 18 in a part corresponding to the aforementioned opening is provided (Panel (f) of FIG. 1). In this biosensor, such part of space which is inside the opening, and surrounded by the working electrode, counter electrode, insulating layer 14, and cover 16, becomes a sample supply port 17 having a capillary structure. This sample supply port 17 is formed as a predetermined space in the region including a reagent loading section at least at the first terminal of the working electrode of the electrode pair. Further, the through hole 18 serves as a vent hole for inhaling a sample by capillary action. Alternatively, it may be a biosensor that is not provided with the insulating layer 14, but the spacer 15 is made of an insulating material to serve also as an insulating layer 14, and such part of space as is sandwiched by the spacer 15 and cover 16 becomes a sample supply port 17 having a capillary structure.

(Method for Producing Biosensor)

The biosensor according to an embodiment of the present invention is produced, for example, in the following manner. That is, on one side of the insulating substrate having a surface with arithmetic mean roughness Ra of approximately 2 $\mu m$, a contact metal is layered by sputtering under the conditions that the pressure of the membrane forming chamber is from 0.1 to 0.5 Pa, the argon gas inflow rate is from 160 to 300 Sccm, and the power is 7800 W. Next, metal layers respectively functioning as the working electrode and the counter electrode are formed by sputtering also under the conditions that the pressure of the membrane forming chamber is from 0.1 to 0.5 Pa, the argon gas inflow rate is from 160 to 300 Sccm, and the power is 8000 W. Next, a reagent preparation solution is coated on the electrode (at least on the first terminal of the working electrode) and dried so that the reagent is provided on the electrode.

An example of a more specific method for producing a biosensor is described below, but the method for producing a biosensor according to an embodiment of the present invention is not limited to the following.

Figure 1:
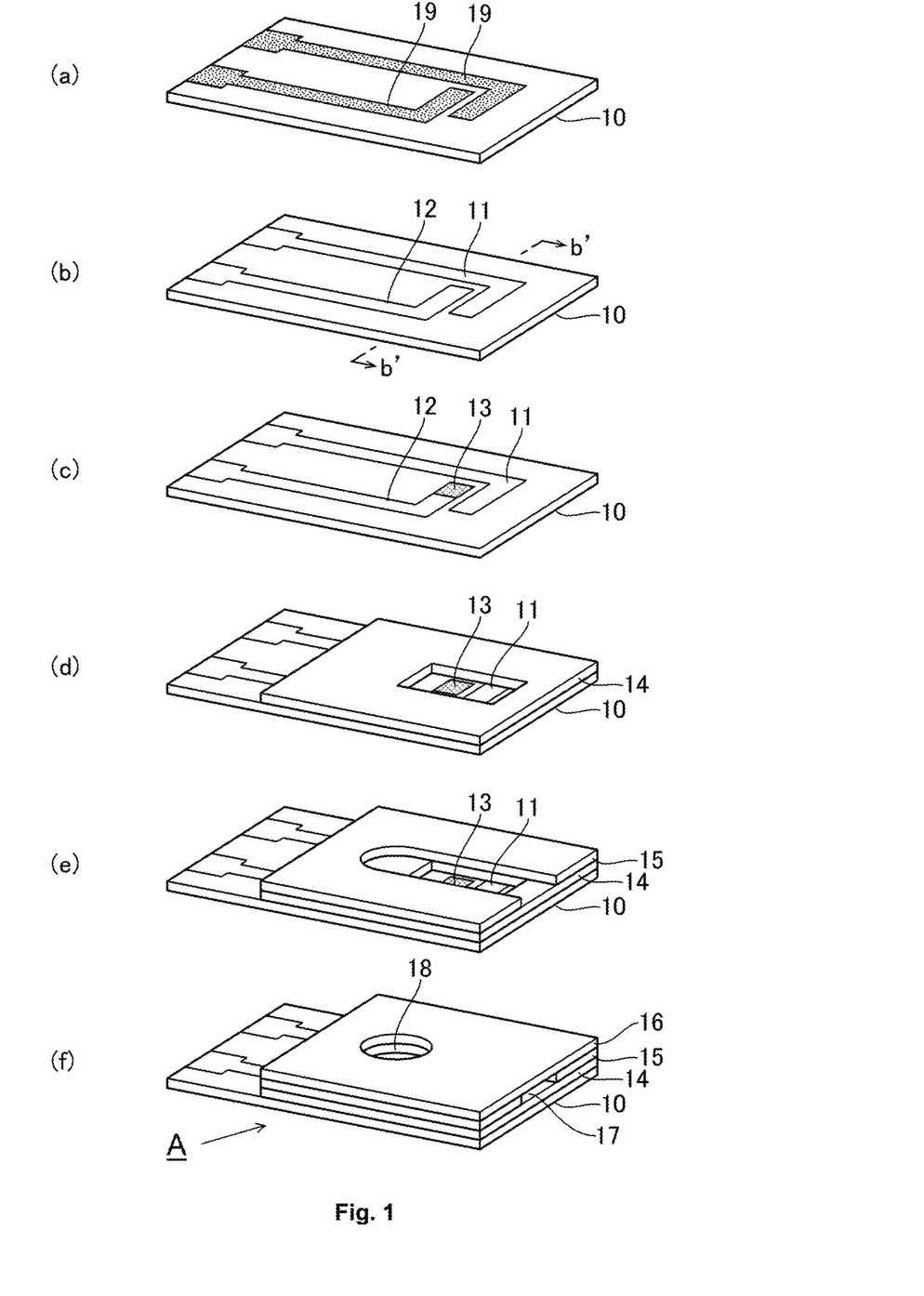
FIG. 1 is a process diagram showing an example of the method for producing a biosensor of one embodiment of the present invention, and panels (a) to (f) show schematic views of the biosensor at each step.

First, as shown in Panel (a) of FIG. 1, a contact metal 19 is coated on a substrate 10 by physical vapor deposition (PVD) by sputtering under the aforedescribed conditions. Next, as shown in Panel (b) of FIG. 1, an electrode system consisting of a counter electrode 11 having a first terminal, a second terminal, and a lead section, and a working electrode 12 having a first terminal, a second terminal, and a lead section is layered on the contact metal 19 by sputtering under the aforedescribed conditions. As the working electrode 12, the nickel alloy is coated on the contact metal.

Figure 2:
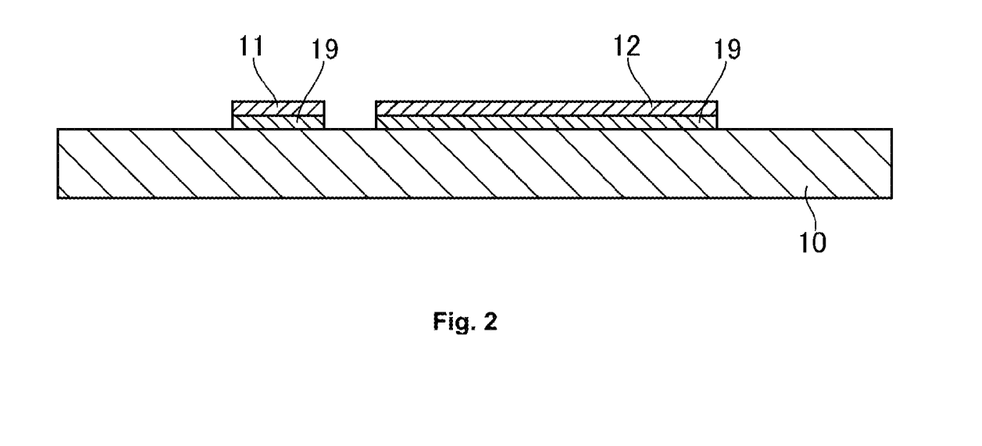
FIG. 2 shows a cross-sectional view of the b'-b' line-cross section in the state (b) in the biosensor manufacturing process shown in FIG. 1.

FIG. 2 shows a cross-sectional view of the b'-b' line-cross section in the state (b) in the biosensor manufacturing process shown in FIG. 1. The contact metal 19 is layered on the substrate 10, and the working electrode 12 and counter electrode 11 are layered on the contact metal 19, respectively.

Coating on the substrate may be performed, besides sputtering, for example, by means of membrane formation by thin membrane plating, other physical vapor deposition method, or chemical vapor deposition (CVD). Subsequently, an electrode system can be formed by performing laser machining, or etching using a mask. For example, a contact metal layer is formed on the insulating substrate by physical vapor deposition, and then a nickel alloy layer is formed on the contact metal layer by physical vapor deposition, followed by partially removing the contact metal and the nickel alloy from the insulating substrate, thereby an electrode group comprising the electrode pair can be formed.

Alternatively, the working electrode 12 can be formed by printing a nickel alloy on the substrate by screen printing or the like.

The counter electrode 11 can also be formed by coating at the same time a counter electrode material on the substrate in the same manner, and performing machining or etching, or by printing the counter electrode material on the substrate by screen printing, or the like.

Next, as shown in Panel (c) of FIG. 1, a reagent is loaded on a part of the working electrode 12, preferably on the first terminal of the working electrode 12. There is no particular restriction on the method of loading the reagent, and, for example, it may be carried out by spotting a solution of the reagent on a part of the working electrode 12, preferably on the first terminal of the working electrode 12, and drying the same. More specifically, the reagent 13 can be formed, for example, by preparing a dispersion of an oxidoreductase, an electron transfer substance, and, if necessary, a buffer, and a binder, dispensing the same onto the working electrode 12, and drying it. As the solvent for preparing the dispersion, for example, water, a buffer, an alcohol, N,N-dimethylformamide (DMF), or dimethyl sulfoxide (DMSO) may be used.

Next, as shown in Panel (d) of FIG. 1, an insulating layer 14 is formed on the substrate 10 where the electrode pair 11 and 12 has been formed. The insulating layer is formed on the lead section of the electrode pair 11 and 12. In other words, the same is formed over the substrate 10 except for the region of the part provided with the reagent in the first terminal of the working electrode 12, and the part of the first terminal of the counter electrode opposing said region. The insulating layer 14 can be formed, for example, by printing an insulating paste in which an insulating resin is dissolved in a solvent on the substrate 10, and then applying a heat treatment or a UV treatment. Examples of the insulating resin include polyester, a butyral resin, and a phenol resin, and examples of the solvent include carbitol acetate, and a dibasic ester mixture solvent (DBE solvent).

Next, as shown in Panel (e) of FIG. 1, a spacer 15 is placed on the insulating layer 14. As illustrated, the spacer 15 has an opening at a position corresponding to a region including the part provided with the reagent of the first terminal of the working electrode 12, and the part of the first terminal of the counter electrode opposing thereto. As a material for the spacer 15, for example, a resin film or tape may be used. When a double-sided adhesive tape is used, it can be easily bonded not only to the insulating layer 14, but also to a cover 16 described below. Further, the spacer may be also formed by means of resist printing, or the like.

Next, as shown in Panel (f) of FIG. 1, a cover 16 is placed on the spacer 15. Although there is no particular restriction on the material for the cover 16, examples thereof include various plastics, and a transparent resin such as PET is preferable. In this regard, a hydrophilic agent (such as shinorine) may be applied to the transparent resin such as PET.

(Use of Biosensor)

The biosensor according to an embodiment of the present invention can be suitably used for a measurement of a measuring target substance in a sample.

(Sample)

Although there is no particular restriction on the sample, insofar as it includes a measuring target substance, a biological sample is preferable, and examples thereof include blood and urine.

(Measuring Target Substance)

Examples of the measuring target substance include glucose, cholesterol, ethanol, sorbitol, fructose, cellobiose, lactic acid, and uric acid.

(Principle of Measurement)

When a sample containing a measuring target substance is brought into contact with the reagent loading section of the first terminal of the working electrode in the biosensor according to an embodiment of the present invention, the measuring target substance reacts with the reagent. When a voltage is applied between the pair of electrodes after the reaction, a signal is generated based on the reaction. By detecting this signal, the measuring target substance can be measured.

Specifically, in a case where the reagent of the biosensor contains an oxidoreductase and an electron transfer substance, electrons generated by an oxidation reaction or a reduction reaction between the oxidoreductase and the measuring target substance are transferred to the electron transfer substance and the electron transfer substance is reduced. When a voltage is applied between the pair of electrodes, a reduced electron transfer substance is oxidized on the surface of the working electrode, and an oxidation current is generated dependent on the amount of the measuring target substance in the sample. By measuring a current value, the concentration of the measuring target substance in the sample can be measured based on the current value.

For determining the concentration of a measuring target substance, the voltammetry method, amperometry method, coulometry method, etc. may be employed. The voltammetry method is a method in which the voltage applied to the electrodes is changed, and the changing pattern of the response current value is measured, and the concentration of a measuring target substance is calculated based on the current peak value, etc. in the pattern. The amperometry method is a method in which a constant voltage is applied to the electrodes, the response current value after a certain time from the start of the reaction is measured, and the concentration of a measuring target substance is calculated based on the response current value. The coulometry method is a method in which a constant voltage is applied to the electrodes such that almost all of the measuring target substance in the sample completes the reaction, then the integrated value of the response current values is obtained, and the concentration of a measuring target substance is calculated based on the integrated value.

(Measuring Method for Measuring Target Substance)

The method for measuring a measuring target substance according to an embodiment of the present invention comprises supplying the sample containing the measuring target substance to the electrode pair mounted on the biosensor, applying a voltage between the pair of electrodes; measuring the value of a current flowing between the pair of electrodes; and calculating the amount of the measuring target substance based on the measured current value.

(Step of Supplying Sample)

Supply of a sample from a container accommodating the sample to the electrode pair of a biosensor can be performed, for example, using a publicly known supply means such as a microchip, a syringe, and a capillary. The supply of a sample can also be performed by an automated supply means.

When a biosensor has the aforedescribed sample supply port, the sample can be efficiently reacted with the biosensor by supplying the sample to the sample supply port.

(Voltage Application Step)

Next, a voltage is applied between the pair of electrodes.

When the amperometry method or the coulometry method is performed, a constant voltage is applied between the pair of electrodes.

In doing so, the voltage applied to the working electrode 12 can be set as appropriate, insofar as it is a voltage positive with respect to the counter electrode, and, for example, it is +50 to +500 mV with respect to the counter electrode, preferably +100 to +250 mV, and especially preferably +200 mV. In the above range of voltage, dissolution of a nickel alloy electrode from the substrate can be suppressed, the stability of the electrode can be maintained, and dissolution of the electrode at the time of voltage application can be prevented, and therefore the background current can be reduced and long-term use becomes possible.

A voltage may be applied to the electrode system after a sample is brought into contact with the reagent, and the system is held in a non-applied state for a predetermined time; or alternatively, the voltage may be applied to the electrode system as soon as a sample is brought into contact with a reagent. In a case where it is held in a non-applied state, the holding time is, for example, 30 sec or less, or 10 sec or less. Meanwhile, when a cyclic voltammetry measurement is performed, the potential with respect to the working electrode is swept at a constant rate. The sweeping cycle of the potential may be plural.

In the case of using a biosensor comprising the first electrode pair and the second electrode pair as described above, the voltage applied to the second electrode pair may be a voltage which is different from that applied to the first electrode pair. For example, in a case where a biosensor equipped with an electrode pair with a structure in which a portion of the reagent is loaded solely on the counter electrode disclosed in WO2005/103669 above, or a biosensor equipped with an electrode pair with a structure in which no reagent is loaded disclosed in Japanese Patent Laid-Open No. 2019-035748 is used for measuring a hematocrit value as the physical value other than the measuring target substance, a high voltage of +1.0 to +7.0 V may be applied to the working electrode of the second electrode pair with respect to the counter electrode of the second electrode pair.

(Current Measurement Step)

As for current measurement, in the case of the amperometry method, the response current value is measured after a predetermined time from the application of voltage, and in the case of the coulometry method, the response current value is measured over time in order to obtain an integrated value of the response current. Meanwhile, in the case of the cyclic voltammetry method, the current value corresponding to the sweeping voltage is continuously measured in order to obtain the cyclic voltammetric waveform. The measurement of the response current value may be performed using an ordinary ammeter or the like.

(Concentration Calculation Step)

The concentration of a measuring target substance is calculated based on the measured response current values.

In the case of the amperometry method, the concentration of a measuring target substance can be calculated by finding in advance the relationship between the response current value and the concentration of the measuring target substance in the form of a calibration curve or the like, and by applying the measured response current value to the calibration curve.

In the case of the coulometry method, the concentration of a measuring target substance can be calculated by finding in advance the relationship between the integrated value of the response current value and the concentration of the measuring target substance in the form of a calibration curve or the like, and by applying the measured integrated value of the response current value to the calibration curve.

In the case of the cyclic voltammetry method, the concentration of a measuring target substance can be calculated by finding in advance the relationship between the peak value of the cyclic voltammetric waveform and the concentration of the measuring target substance in the form of a calibration curve or the like, and by applying the measured response current value to the calibration curve.

[Measurement Device]

According to an embodiment of the present invention, the biosensor according to an embodiment of the present invention is utilized as incorporated in a measurement device. The measurement device may include a control unit 22 for controlling the potential, a potentiostat 25, a detection unit 24 for detecting the current, an arithmetic processing unit 23 for calculation from the current value, an output unit 21 for measuring the measurement result, and a plurality of connection terminals 26. It may additionally include a power supply unit for applying a voltage to the pair of electrodes of the biosensor.

Next, an embodiment of the measurement device in which a measurement is performed with the biosensor according to an embodiment of the present invention will be described by way of the drawings. Here, an example embodiment of the measurement device equipped with a glucose sensor is presented, however, the measurement device equipped with the biosensor according to an embodiment of the present invention is not limited to this embodiment.

FIG. 2 shows an example configuration of the measurement device B. The measurement device B includes a control computer 20 and a potentiostat 25, and when the biosensor A is mounted, each of connection terminals 26 is electrically connected to either of the respective second terminals of the working electrode and the counter electrode of the biosensor. As for the hardware aspect of the control computer 20, it includes a processor such as a CPU (Central Processing Unit), a storage medium such as a memory (RAM (Random Access Memory), or ROM (Read Only Memory)), and a communication unit. When the processor loads the program stored in the storage medium (e.g., ROM) onto the RAM and executes the same so that it functions as a device equipped with an output unit 21, a control unit 22, an arithmetic processing unit 23, and a detection unit 24.

The control unit 22 controls the timing of voltage application, the value of applied voltage, etc. The potentiostat 25 is a device that keeps the potential of the working electrode constant with respect to the counter electrode, and is controlled by the control unit 22 to apply a predetermined voltage (50 mV to 500 mV) between the working electrode and the counter electrode of the biosensor A, to measure the response current of the working electrode, and to send the measurement result of the response current to the detection unit 24.

The arithmetic processing unit 23 calculates the concentration of a measuring target substance from the detected current values and stores it. The output unit 21 performs data communication with the display unit, which is not illustrated, and sends the calculation result of the concentration of the measuring target substance obtained by the arithmetic processing unit 23 to the display unit.

An embodiment of the method of using this measurement device will be described below referring to an example in which the sample is whole blood, the measuring target substance is glucose, the oxidoreductase is glucose dehydrogenase, and the electron transfer substance is a ruthenium (III) compound.

Figure 3:
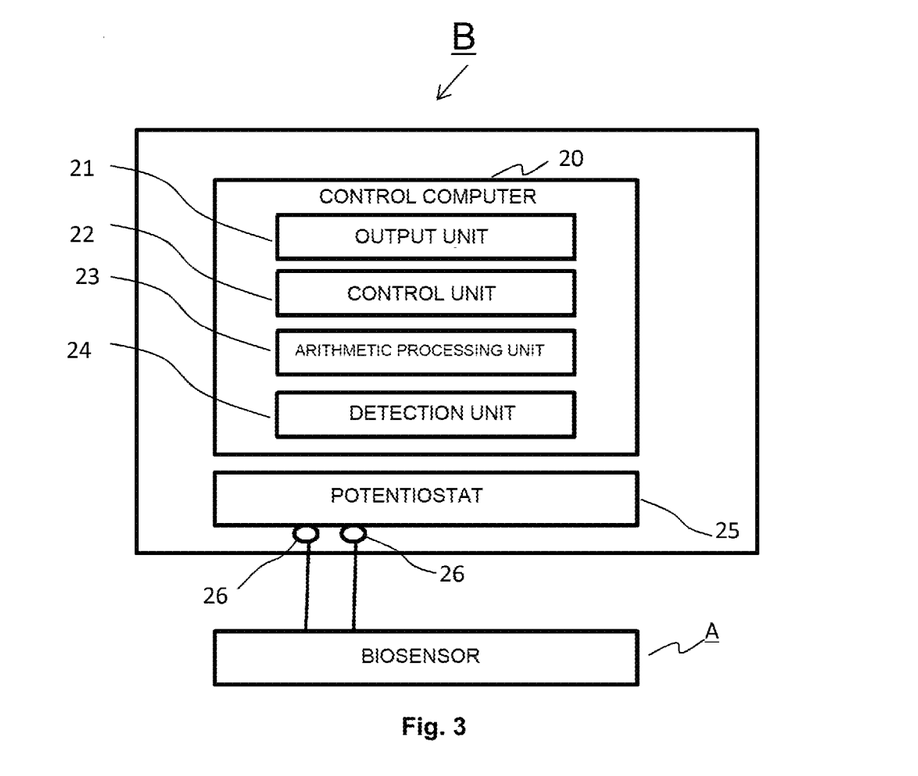
FIG. 3 is a schematic diagram of one embodiment of a measurement device equipped with the biosensor according to one embodiment of the present invention.

FIG. 3 is a flowchart showing an example of the measurement process for the glucose concentration using the measurement device.

First, the biosensor A is mounted on the measurement device, and then a sample containing the measuring target substance is supplied to the electrode pair in the biosensor A (sample supply step).

Specifically, for example, the whole blood sample is brought into contact with one end of the sample supply port 17 of the biosensor A. Since this sample supply port 17 has a capillary structure as described above, and there is a vent hole 18 at a position corresponding to the other end in the cover 16, the sample is sucked inward by capillary action. The sucked sample will reach the reagent surface provided on the working electrode 12 in the detection unit 13. Glucose in the sample that has reached the surface reacts preferentially with glucose dehydrogenase and is converted to gluconolactone. The electrons generated in this process reduce a ruthenium (III) compound to form a ruthenium (II) compound.

Next, a voltage is applied between the pair of electrodes (voltage application step).

Specifically, for example, when the CPU (control unit 22) of the control computer 20 receives a direction to start a measurement of the glucose concentration, the control unit 22 controls the potentiostat 25 to apply a predetermined voltage to the working electrode, and starts the measurement (Step S01). This may be interpreted as a direction to start a concentration measurement.

By applying a positive voltage to an electrode, electron transfer takes place between the ruthenium (II) compound present in the reagent and the electrode so that a response current flows, which is to be detected (response current measurement step).

Specifically, for example, the potentiostat 25 measures the response current obtained by the voltage application, that is the current based on the transfer of electrons derived from the measuring target substance (glucose) in the sample to the electrode, for example, the steady state current after 1 to 20 sec from the voltage application, and sends the value to the detection unit 24 (Step S02).

Since the value of this oxidation current is proportional to the concentration of glucose in the sample, the concentration of glucose in the sample can be calculated by converting the value to a glucose concentration by the above arithmetic processing means (concentration calculation step).

Specifically, for example, the arithmetic processing unit 23 calculates the glucose concentration by performing an arithmetic processing based on the current value (Step S03). For example, the arithmetic processing unit 23 of the control computer 20 has in advance a calculation formula for glucose concentration, or a calibration curve data with respect to glucose concentration, and calculates the glucose concentration by converting the current value into a glucose concentration using the calculation formula, or the calibration curve.

The output unit 21 sends the calculation result of the glucose concentration to the display unit 25 through the communication link formed between this unit and the display unit 25 (Step S04). It is also possible to store the calculation result in the arithmetic processing unit 23 and to call the calculation result later to display the same for confirming in the display unit.

EXAMPLES

The invention will be described more specifically below by way of Examples, but the invention is not limited to the following embodiments.

Example 1

For comparing the current response performance of each metal of each electrode of the biosensor, a biosensor produced according to the following procedure, which was simpler compared to the biosensor illustrated in FIG. 1 was used. First, a PET substrate (length: 50 mm, width: 6 mm, thickness: 250 m) was prepared as the insulating substrate 10 of a glucose sensor, and some of a variety of metals (gold (Au), nickel (Ni), Ni—V (92/8), Ni—W (81/19), or Ni—Ru (50/50)) were sputtered on the entire surface of one side of the substrate, and by trimming the same, a working electrode 12 having the first terminal, the second terminal, and the lead section, and a counter electrode 11 having the first terminal, the second terminal, and the lead section, were formed.

On the working electrode 12, only one of the electron transfer substance, i.e., a ruthenium compound ([Ru(NH$_3$)$_6$]Cl$_3$, produced by Dojindo Laboratories), or potassium ferricyanide, was loaded. Specifically, 0.45 μL of the above electron transfer substance was dispensed onto the first terminal of the working electrode 12. Then, the same was dried at 30° C. to complete loading of the electron transfer substance.

Next, a spacer was placed on the electrode pair through an adhesive tape to secure a predetermined space. Since the predetermined space at the opening of the spacer comes to have a capillary structure, this was used as the sample supply port.

Meanwhile, glucose oxidoreductase may be used as the reagent, and in this case glucose dehydrogenase may be used. When glucose dehydrogenase was used, a preparation solution for making the reagent was prepared as follows. First, glucose dehydrogenase (3.0 U/strip) was added to 10 mM or 50 mM of a ruthenium compound ([Ru(NH$_3$)$_6$]Cl$_3$, produced by Dojindo Laboratories), or 10 mM or 50 mM of potassium ferricyanide to prepare a preparation solution for making the reagent.

<Cyclic Voltammetry Voltammetric Measurement>

Figure 4:
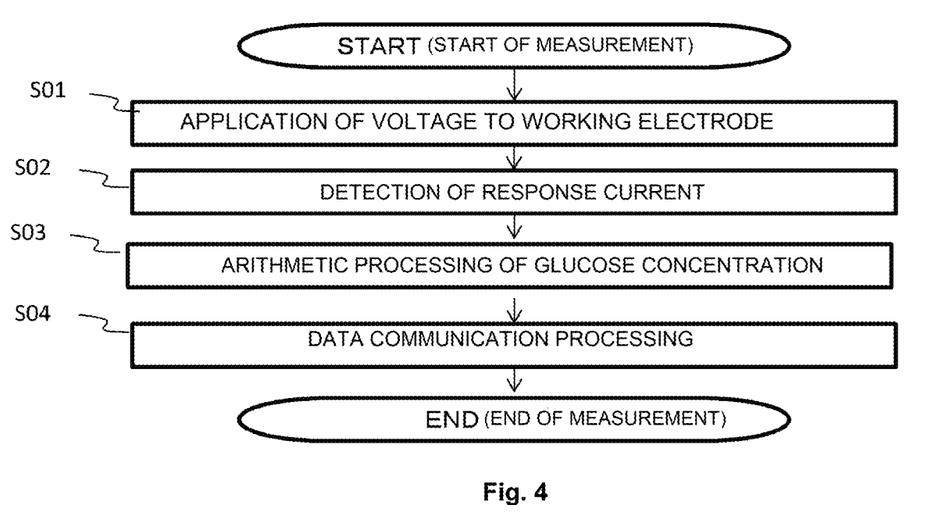
FIG. 4 is a flow chart illustrating one embodiment of a measurement program using the measurement device equipped with the biosensor according to one embodiment of the present invention.

With respect to a biosensor equipped with an electrode (working electrode) made of Au, Ni, or any of various Ni alloys, containing the electron transfer substance prepared as described above in the reagent, the electrode response characteristics were evaluated by measuring the electrical responsiveness of the electron transfer substance through examination of the cyclic voltammetric waveform. The cyclic voltammetric waveform was examined by introducing a sample (100 mM PBS (phosphate buffered saline), pH 7.0) into the sample supply port of the glucose sensor, sweeping the voltage applied to the working electrode at a sweep rate of 20 mV/sec between −400 mV and +400 mV with respect to the counter electrode in the case of the ruthenium complex, and between −800 mV and +800 mV in the case of ferricyanide ferricyanide for 3 cycles, and measuring the response current during the sweeping. FIG. 4 shows the calculation results of mean values of the peak current values in the first, second and third cycles with respect to each biosensor.

As a result, it was found that any of a Ni—V electrode, a Ni—W electrode, and a Ni—Ru electrode, when used as a working electrode, showed superior current responsiveness compared to a Ni electrode, although not as good as an Au electrode. Namely, it was found that the responsiveness of an electron transfer substance close to that of a noble metal electrode can be obtained, when any one of nickel alloy electrode selected from a Ni—V electrode, a Ni—W electrode, or a Ni—Ru electrode was used as the working electrode of the biosensor. Consequently, by using such a nickel alloy, a biosensor that is able to measure a measuring target substance such as glucose with high reproducibility can be produced inexpensively and easily.

Example 2

Next, the effect of a buffer used in the reagent of the electrode on the background was investigated. For comparing the performances of buffers, the same biosensor as the biosensor of Example 1 simply except that a reagent (an electron transfer substance, and an oxidoreductase) was not loaded on the first terminal of the working electrode 12 of the detection unit 13 was used. That is, for a Ni—V electrode, a Ni—W electrode, or a Ni electrode, citric acid was used as a buffer in a sample (final concentration 20 mM, 50 mM, 100 mM, or 200 mM), and cyclic voltammetry (from 0 to +1.0 V) was performed, and the current value at +0.5 V, which was a voltage suitable for grasping the characteristics, was measured. As Comparative Example, the current value was measured using the similar measurement method but phosphoric acid was used as a buffer in a sample (final concentration 20 mM, 50 mM, 100 mM, or 200 mM). In this experiment, since only the buffer is present on the detection unit 13 of the electrode, the current value obtained by applying a voltage is attributed solely to the current value from the solution containing only the buffer. From this, the effect of the background of each buffer, namely the noise component can be evaluated. The results are shown in Table 1. As a result, it was found that when a citrate buffer was used, the background current value could be reduced compared to a case where a phosphate buffer was used, and such tendency was significant for a Ni—V electrode. One of the causes of the background current is conceivably corrosion of an electrode caused by the application of voltage. This is because Ni and V (vanadium) are base metals and easily corroded. When a citrate buffer was used, citric acid formed a complex with Ni, which conceivably inhibited destruction of a passive film to reduce the background current value. Since this effect is dependent on the concentration of citric acid, the same effect can be obtained, even when a phosphate citrate buffer is used. Further, since the higher the concentration, the lower the background current value becomes, it can be known that even at a citrate concentration higher than 200 mM, for example, in a range of 200 mM to 300 mM, the same effect can be obtained.

TABLE 1

| Relationship between citrate or phosphate and background current value (μA) at various electrodes | | | | | | | | |
|---|---|---|---|---|---|---|---|---|
| | 200 mM | | 100 mM | | 50 mM | | 20 mM | |
| | Citrate | Phosphate | Citrate | Phosphate | Citrate | Phosphate | Citrate | Phosphate |
| Ni-V | 0.551 | 0.898 | 0.651 | 0.941 | 0.627 | 0.770 | 1.086 | 1.164 |
| Ni-W | 0.082 | 0.125 | 0.091 | 0.108 | 0.096 | 0.098 | 0.097 | 0.090 |
| Ni | 0.383 | 0.772 | 0.345 | 0.730 | 0.328 | 0.590 | 0.266 | 0.408 |

Example 3

Figure 5A:
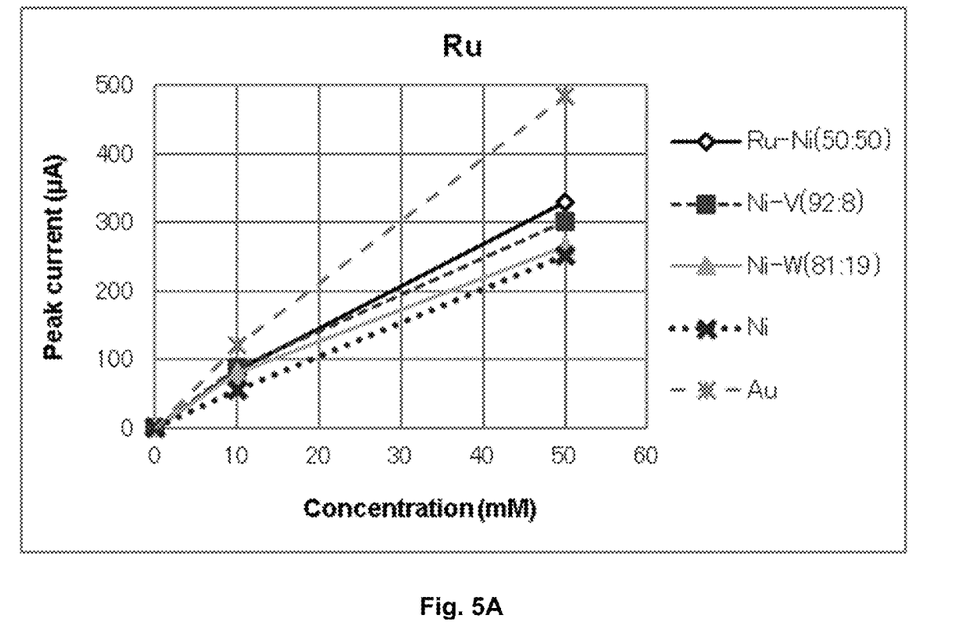
FIG. 5A is graphs showing the measurement results of peak current values obtained by cyclic voltammetry performed using a biosensor containing an electron transfer substance (ruthenium complex) in a reagent, and equipped with an electrode pair composed of Au, Ni, or any of various Ni alloys. The measurements were performed using electrodes with different concentrations of the electron transfer substance, and the peak current values were plotted.
Figure 5B:
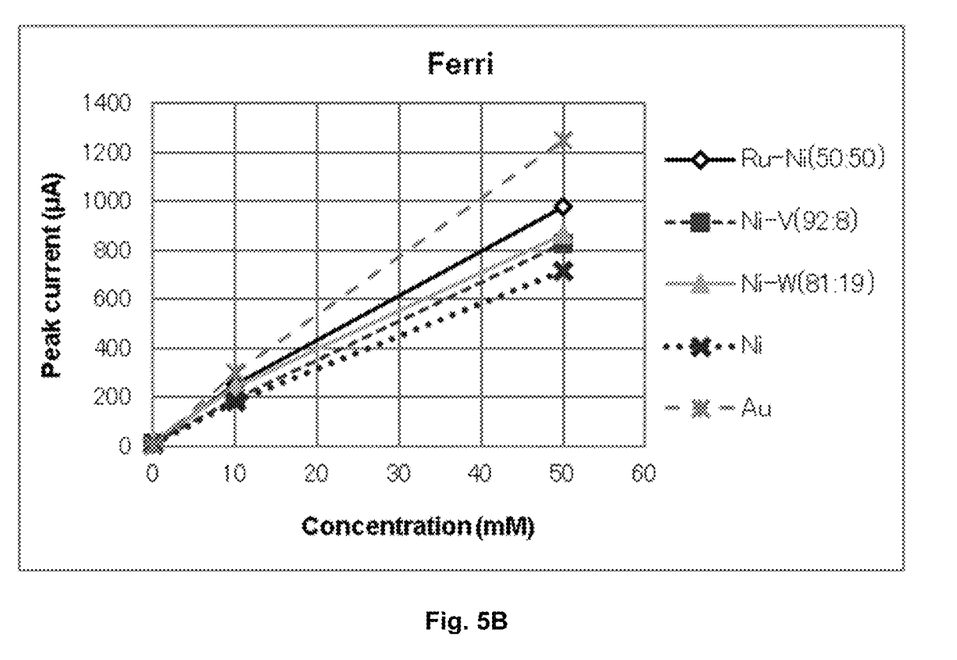
FIG. 5B is graphs showing the measurement results of peak current values obtained by cyclic voltammetry performed using a biosensor containing an electron transfer substance (ferricyanide) in a reagent, and equipped with an electrode pair composed of Au, Ni, or any of various Ni alloys. The measurements were performed using electrodes with different concentrations of the electron transfer substance, and the peak current values were plotted.

Next, the reproducibility of glucose concentration measurement was examined. The same biosensor (biosensor shown in FIG. 1 having a Ni—V electrode as the working electrode) as the biosensor in Example 1, except that the electrodes were solely Ni—V electrodes, and the reagent with the composition shown in the following Table 2 was loaded on the first terminal of the working electrode, was used, and the respective detection sensitivities with different buffers at the Ni—V electrode were examined. As a buffer phosphate, citrate, citrate phosphate, PIPES, and HEPES (pH 7.0, respectively) were used. The amount of each buffer was adjusted such that its concentration in a mixed solution of the reagent and a sample on the working electrode became approximately 100 mM, when the reagent was dissolved in a sample. In the case of citrate, or citrate phosphate, the amount of citrate present per strip was set at 17.2 μg. This corresponds to 90 nmol in terms of the amount of substance of citrate, and since the partial area on the working electrode where the reagent is loaded is 0.006 cm$^2$, the molar concentration of citric acid corresponds to 15 μmol/cm$^2$. Using the measurement device shown in FIG. 3 with such a biosensor, measurements were performed on a venous whole blood specimen, while changing the glucose concentration to 0 mg/dL, 67 mg/dL, 134 mg/dL, 336 mg/dL, 600 mg/dL, and 1000 mg/dL, by applying a voltage of +0.2 V to the working electrode, and measuring a current value 8 sec after the voltage application. The results are shown in FIG. 5A and FIG. 5B.

TABLE 2

Composition of reagent in Example 3

|  | Amount present per strip |
|---|---|
| Poly(vinyl alcohol) (PVA) | 1.35 μg |
| 1-Methoxy-5-ethylphenazinium ethylsulfate (1m-PES) | 0.0594 μg |
| Ru(NH$_3$)$_6$Cl$_3$ | 14.0 μg |
| Neo Protein Saver (made by Toyobo) | 0.378 μg |
| sucrose laurate | 0.905 μg |
| GDH(AMANO (Lot GDHP1252601)) | 2.7 Unit |
| Each buffer (pH7.0) | (Adjusted to approximately 100 mM when dissolved) |

As a result, it became clear that when an electrode with a citrate buffer, or a phosphate citrate buffer was used, high response current values corresponding to the glucose concentration were obtained as in the case of phosphate, and the linearity of the response current values was excellent. On the other hand, when PIPES or HEPES was used, the linearity of the response current values with respect to the glucose concentration was lowered and it was found that the reproducibility in glucose concentration measurement significantly deteriorated. This phenomenon was caused by the lowered solubility of a specimen in a reagent for which PIPES or HEPES was used.

Figure 6:
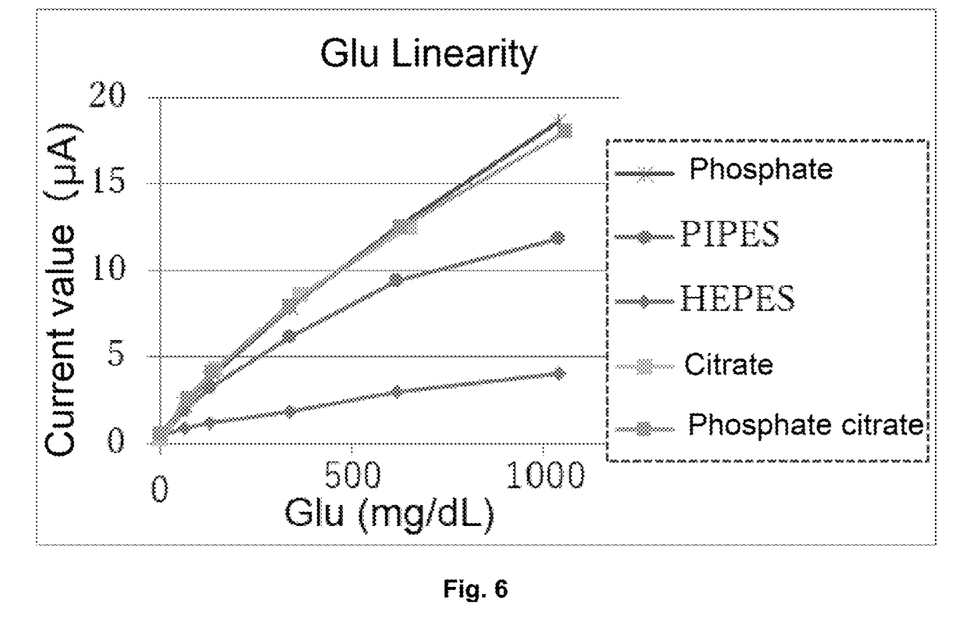
FIG. 6 is a graph showing the results of an examination concerning the relationship between the glucose concentration and the current value, in which the measurement was performed using a biosensor with an electrode using each of various buffers (200 mM) as a reagent.

Next, using the same data, the results of the slope of the calibration curve into the low glucose concentration range (Glu 0-Glu 67) and the medium glucose concentration range (Glu 67-Glu 134) are separately shown in FIG. 6.

Figure 7:
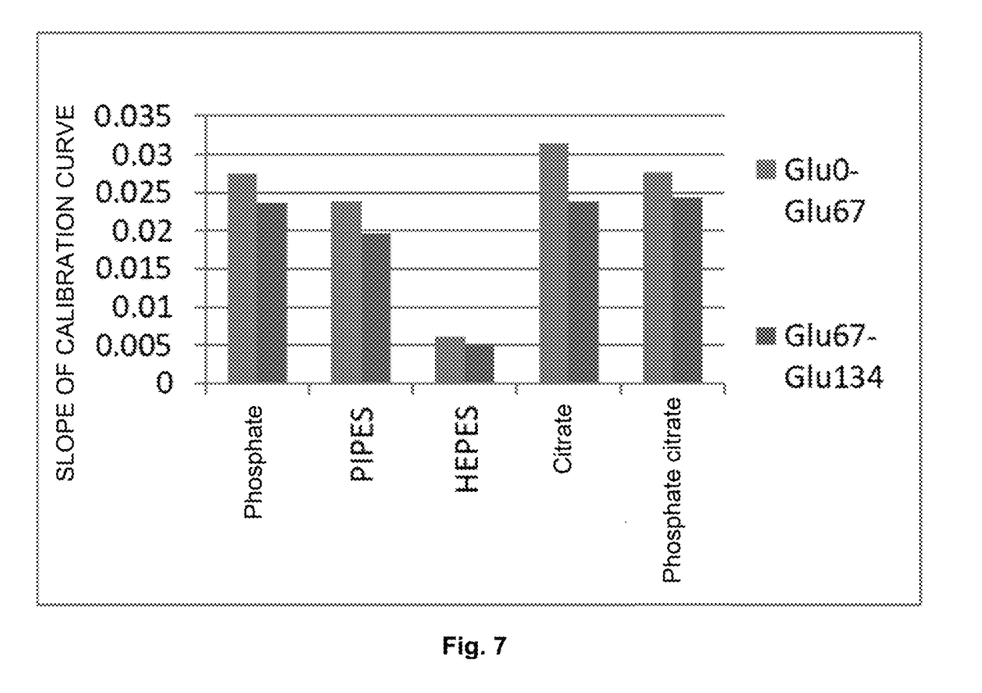
FIG. 7 is a graph showing the results of an examination of the slopes in the graph of FIG. 6 in a low concentration range (0 to 67 mg/dL) and a high concentration range (67 to 134 mg/dL) of glucose.

Along the horizontal axis of FIG. 6, the buffers with phosphate, citrate, phosphate citrate, PIPES, and HEPES, respectively for the low glucose concentration range and for the medium glucose concentration range, are aligned, and the respectively corresponding slopes of the calibration curves are indicated along the vertical axis. The larger slope of the calibration curve means that the reproducibility of the calculated glucose concentration value is higher and the detection sensitivity is higher. It has been found from FIG. 7 that, when an electrode with a reagent containing a citrate buffer or a phosphate citrate buffer is used, the slope in the low concentration range is larger than the case with a phosphate, and both the slopes in the low concentration range and the medium concentration range are larger than the case with PIPES or HEPES. Consequently, it becomes clear that an electrode with a reagent containing a citrate buffer, or a phosphate citrate buffer has higher detection sensitivity in the low glucose concentration range.

Further, using the same biosensor, samples (whole blood) with glucose concentrations of 67 mg/dL, 134 mg/dL, and 336 mg/dL were measured (n=10), and the respective coefficients of variation (CV) were determined. The results are shown in Table 3. As a result, it was found that the measurement by a biosensor having an electrode using a citrate buffer or a phosphate citrate buffer exhibited superior reproducibility of measurement in the low glucose concentration range.

TABLE 3

Relationship between kinds of buffer and CV (%)

|  | Glu 67 | Glu 134 | Glu 336 |
|---|---|---|---|
| Phosphate | 2.10 | 1.87 | 1.74 |
| PIPES | 15.99 | 16.67 | 11.97 |
| HEPES | 9.46 | 21.25 | 10.77 |
| Citrate | 0.93 | 2.55 | 2.81 |
| Phosphate citrate | 1.22 | 1.87 | 1.94 |

When PIPES or HEPES was used, it was confirmed, from an experiment which is similar to Example 2 but not further described herein, the effect of background components was not so strong. From the experiments in Example 3, the slopes of the calibration curves were small and the CV values were large, indicating that the high detection sensitivity and measurement reproducibility were specific to citrate.

As described above, when a citrate buffer or a phosphate citrate buffer is used in a reagent, the background current value can be reduced, and the reproducibility of the measurement can be enhanced. The above enables a measurement with high reproducibility and high accuracy.

A new problem has been found in a measurement using the biosensor according to an embodiment of the present invention. Namely, under a condition with a high current value, specifically when a high voltage as high as 1.0 V or more is applied, or when a specimen with a low resistance value (i.e., current flows easily) such as blood plasma is used, a nickel alloy, which is a base metal, dissolves out to cause detachment of an electrode from the substrate, or pore formation in an electrode, and as a result, a correct response current value can be hardly obtained. It is also found that this phenomenon occurs more significantly when the electrode of a biosensor is thicker, and/or the contact metal is thinner. Particularly, it has been confirmed that the phenomenon occurs more significantly when a biosensor comprising the first electrode pair and the second electrode pair and both of which are composed of a contact metal and a nickel alloy and the second electrode pair having a structure in which a portion of the reagent is loaded solely on the counter electrode, or having a structure in which no reagent is loaded, is used for measuring a hematocrit value, and a high voltage of +1.0 to +7.0 V is applied.

In view of the above, as shown in Example 4 below, by using a biosensor having an electrode system prepared by forming a contact metal layer consisting of titanium on an insulating substrate and layering a nickel-vanadium alloy on the contact metal, response current value was evaluated while changing the thickness of both the contact metal layer and the nickel-vanadium layer. As a result, it was found that the aforedescribed phenomenon can be prevented when the thicknesses of both the electrode and the contact metal are set to be within predetermined ranges, and to hold a certain relationship between them. That is, we have affirmed at least the following four requirements.

(1) The thinner an electrode is, the more stable the electrode layer becomes, however, if it is too thin, the resistance value of the electrode itself becomes too high, or the variation in resistance value among individual electrodes becomes too large. Therefore, a thickness above a certain level is necessary.

(2) Since the purpose of the contact metal is to fix the electrode to the substrate, a certain thickness is necessary for stabilizing the electrode layer, however, when it is too thick, it becomes unstable.

(3) The total thickness of the electrode and the contact metal should be at least 10 μm in order to be unaffected by the ruggedness of the substrate (when it is too thin, the surface of the electrode will be rugged and the resistance value will become high).

(4) Up to a certain level, as the thickness of the contact metal increases, the thickness of an electrode that can be placed thereon increases, however, when it exceeds a certain level, the measured value will be affected and the thickness of an electrode that can be placed thereon will be reduced. Therefore, the total thickness should be 55 μm or less.

In a case where the electrode is made of a nickel-vanadium alloy, and the contact metal is made of titanium, it was found that the aforedescribed phenomenon can be prevented by satisfying the following conditions, where the thickness of the titanium is represented by x, and that of the nickel-vanadium alloy by y as in Example 4.

1) $7\ \mu m \leq x \leq 52\ m$
2) $3\ \mu m \leq y \leq 25\ m$
3) $y = -11/16x + 155/4$ Example 4

A biosensor was prepared by layering a contact metal consisting of titanium on an insulating substrate and then layering a nickel-vanadium alloy on the contact metal to form an electrode pair both of which do not contain reagents. Several biosensors were prepared with different thicknesses of contact metal and nickel-vanadium alloy, and the response current was evaluated by adding the sample shown below and then applying a voltage thereto.

<Measurement Condition>
Voltage: 3.5 V
Voltage application time: 10 sec
Temperature: 40° C.
Sample: Blood with a hematocrit value of 20%.

Figure 8:
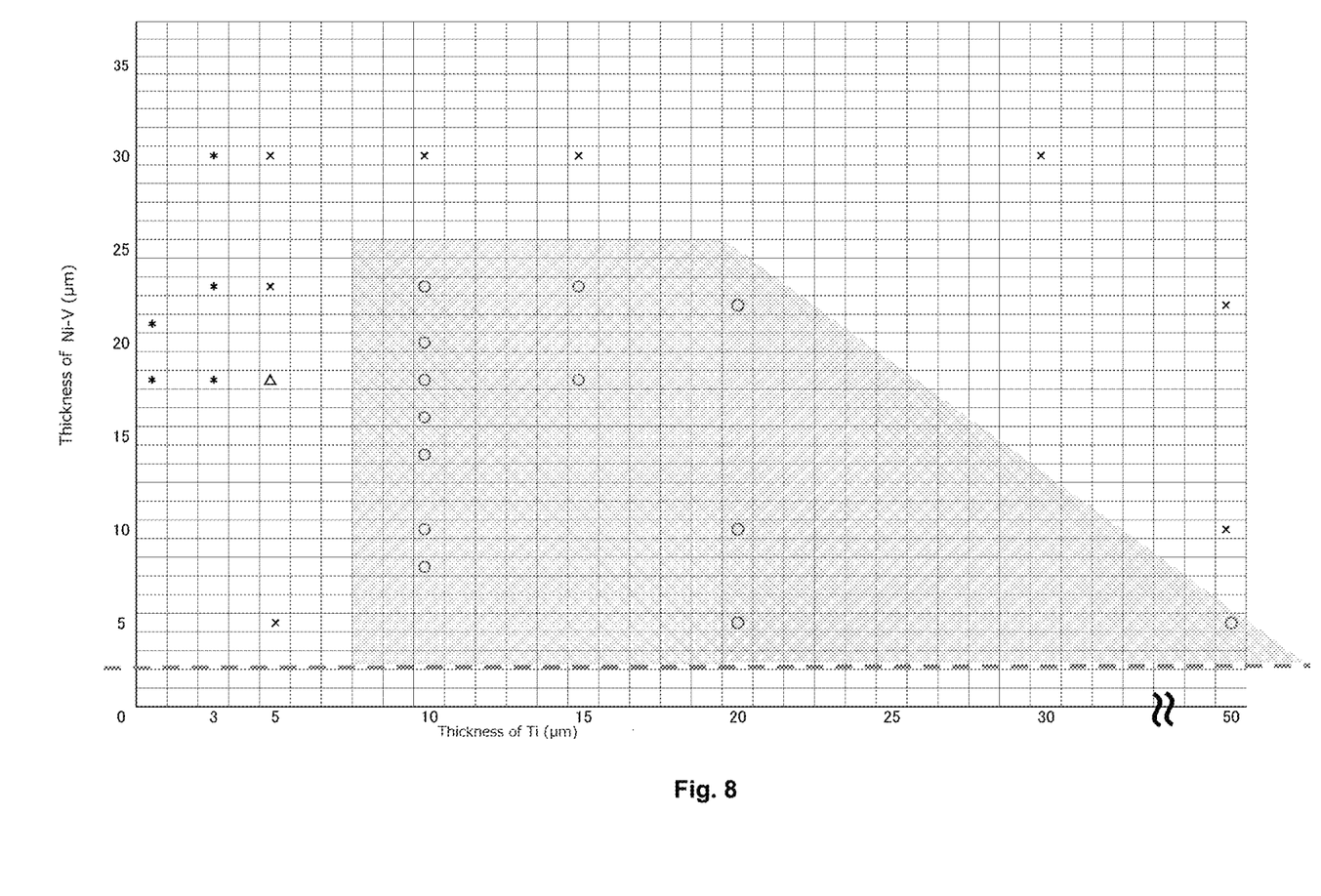
FIG. 8 shows the results of the examination of the response current value when the thickness of each of a nickel-vanadium alloy and titanium is changed in the biosensor in which an electrode was formed by layering a nickel-vanadium alloy on a contact metal made of titanium. The symbols represent the followings.

<Evaluation Criteria of Verification Results>
* Sudden decrease in the response current value occurred within 5 sec
x Premature hike in the response current value occurred within 5 sec
Δ The variation of the 5-sec values of the response current value is 20 μA or more.
○ No problem The results are shown in FIG. 8.

Hereinafter, the results in FIG. 8 are discussed. Before conducting the experiment shown in FIG. 8, we first observed the biosensors fabricated under the respective electrode and contact metal thickness conditions, and visually checked the surface irregularities of the electrodes. As a result, as shown in the above phenomenon (3), when the total thickness of the nickel-vanadium alloy and contact metal was less than 10 μm, the biosensor was affected by the unevenness of the substrate, which was expected to affect the measurement results and was judged to be inappropriate as a biosensor.

Thus, several biosensors with a total thickness of 10 μm or more of nickel-vanadium alloy and contact metal were fabricated without being affected by the unevenness of the substrate, and the results according to the measurement conditions are shown in FIG. 8. From the results in FIG. 8, it was confirmed that the measurement was stable even under such thickness conditions when the thickness of the nickel-vanadium alloy was more than 3 μm and less than 25 μm, and when the thickness of the titanium was more than 7 m and less than 20 μm. This confirmed that there were thickness conditions for the electrode and contact metal as described in the above phenomena (1) and (2). On the other hand, under the condition that the thickness of titanium was 20 μm or more, the thicker the titanium was, the thinner the nickel-vanadium alloy placed on top of it became. It was confirmed that the measurement could be performed when the titanium was 50 m and the nickel-vanadium alloy was 5 μm, and the relation of the formula 3) $y = -11/16x + 155/4$ could be found and confirm the condition of phenomenon (4) above.

REFERENCE SIGNS LIST

A Biosensor
10 Substrate
11 Counter electrode
12 Working electrode
13 Reagent
14 Insulating layer
15 Spacer
16 Cover
17 Sample supply port
18 Vent hole
19 Contact metal
B Measurement device
Control computer
21 Output unit
22 Control unit
23 Arithmetic processing unit
24 Detection unit
Potentiostat
26 Connection terminal While the invention has been described in detail with reference to exemplary embodiments thereof, it will be apparent to one skilled in the art that various changes may be made, and equivalents employed, without departing from the scope of the invention. Each of the aforementioned documents as well as JP 2020-058700 is incorporated by reference herein in its entirety.

What is claimed is:

1. A biosensor for measuring a measuring target substance in a sample comprising:
   an insulating substrate;
   an electrode pair provided on the insulating substrate; and
   a reagent that comprises an oxidoreductase and an electron transfer substance and is provided at least on a working electrode of the electrode pair,
   wherein the working electrode comprises a nickel-vanadium alloy, and
   wherein the weight ratio of nickel to vanadium of the nickel-vanadium alloy is from 80/20 to 95/5.

2. The biosensor according to claim 1, wherein the weight ratio of nickel to vanadium of the nickel-vanadium alloy is from 85/15 to 95/5.

3. The biosensor according to claim 1, wherein the weight ratio of nickel to vanadium of the nickel-vanadium alloy is from 90/10 to 94/6.

4. The biosensor according to claim 1, wherein the electron transfer substance is a ruthenium complex or a ferricyanide.

5. The biosensor according to claim 1, wherein the reagent comprises a citrate buffer or a phosphate citrate buffer.

6. The biosensor according to claim 5, wherein the concentration of the citrate in the reagent is from 1.5 µmol/cm² to 22 µmol/cm² at the part on the working electrode on which the reagent is provided.

7. The biosensor according to claim 1, wherein the oxidoreductase is glucose dehydrogenase and the measuring target substance is glucose.

8. The biosensor according to claim 1, wherein
a contact metal is layered on the insulating substrate,
the nickel-vanadium alloy is layered on the contact metal to form the working electrode, and
the total thickness of the nickel-vanadium alloy and the contact metal that form the working electrode is from 10 µm to 55 µm.

9. The biosensor according to claim 8, wherein, when the contact metal is made of titanium and the titanium and the nickel-vanadium alloy satisfy the following thickness conditions,
1) 7 µm≤x≤52 µm
2) 3 µm≤y≤25 µm
3) y=−11/16x+155/4
wherein x stands for the thickness of the titanium, and y stands for the thickness of the nickel-vanadium alloy.

10. The biosensor according to claim 9, wherein
electrodes including the electrode pair is formed by
layering the contact metal on the insulating substrate by physical vapor deposition,
layering the nickel-vanadium alloy on the contact metal by physical vapor deposition, and
partially removing the contact metal and the nickel-vanadium alloy from the insulating substrate.

11. A method for measuring a measuring target substance comprising:
supplying the sample containing the measuring target substance to the electrode pair mounted on the biosensor according to claim 1;
applying a voltage between the pair of electrodes;
measuring the value of a current flowing between the pair of electrodes; and
calculating the amount of the measuring target substance based on the measured current value.

12. The method according to claim 11, wherein the voltage applied to the working electrode is a voltage of +50 mV to +500 mV relative to the counter electrode of the electrode pair.

* * * * *